United States Patent
Schoepp

(10) Patent No.: US 7,736,371 B2
(45) Date of Patent: Jun. 15, 2010

(54) TRAJECTORY GUIDE

(75) Inventor: Hans Schoepp, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 424 days.

(21) Appl. No.: 11/698,445

(22) Filed: Jan. 26, 2007

(65) Prior Publication Data

US 2008/0183191 A1    Jul. 31, 2008

(51) Int. Cl.
*A61B 19/00* (2006.01)

(52) U.S. Cl. .................................. 606/130; 604/104

(58) Field of Classification Search ............... 606/130, 606/57, 105, 246, 184, 204, 99, 186, 190, 606/90, 61, 266, 129, 167; 600/196, 201, 600/214, 219, 225, 235, 244, 417, 429, 205, 600/433, 102, 210, 407; 81/367; 128/303, 128/92; 623/17.15; 604/104

See application file for complete search history.

(56) References Cited

U.S. PATENT DOCUMENTS

| | | | | |
|---|---|---|---|---|
| 4,050,464 A * | 9/1977 | Hall | .......................... | 606/86 A |
| 4,271,836 A * | 6/1981 | Bacal et al. | ................ | 606/86 A |
| 5,054,497 A | 10/1991 | Kapp et al. | | |
| 5,201,742 A | 4/1993 | Hasson | | |
| 5,562,680 A * | 10/1996 | Hasson | ........................ | 606/119 |
| 5,776,144 A * | 7/1998 | Leysieffer et al. | ............. | 606/130 |
| 5,951,564 A * | 9/1999 | Schroder et al. | ............. | 606/100 |
| 5,984,922 A * | 11/1999 | McKay | ....................... | 606/86 A |
| 6,080,134 A | 6/2000 | Lotti et al. | | |
| 6,110,182 A * | 8/2000 | Mowlai-Ashtiani | .......... | 606/130 |
| 6,746,459 B2 * | 6/2004 | Kato | ............................ | 606/153 |
| 6,755,841 B2 * | 6/2004 | Fraser et al. | .................... | 606/99 |
| 6,782,288 B2 | 8/2004 | Truwit et al. | | |
| 6,863,679 B1 * | 3/2005 | Aaron | .......................... | 606/210 |
| 2002/0045904 A1 * | 4/2002 | Fuss et al. | ...................... | 606/99 |
| 2003/0055436 A1 | 3/2003 | Daum et al. | | |
| 2003/0114876 A1 | 6/2003 | Samset et al. | | |
| 2004/0167543 A1 | 8/2004 | Mazzocchi et al. | | |
| 2005/0038511 A1 * | 2/2005 | Martz et al. | .............. | 623/17.11 |

FOREIGN PATENT DOCUMENTS

WO    WO 2006/102085    9/2006

OTHER PUBLICATIONS

International Search Report and Written Opinion in PCT/IB2008/000328 dated Jul. 22, 2008.

* cited by examiner

*Primary Examiner*—Anhtuan T Nguyen
*Assistant Examiner*—Tin Nguyen
(74) *Attorney, Agent, or Firm*—McCracken & Frank LLP

(57) ABSTRACT

A trajectory guide includes a guide body defining a selected trajectory through an entry aperture or opening, engagement surfaces for insertion into the entry aperture, and a fixing mechanism coupling the guide body with the engagement surfaces. The engagement surfaces may be easily fixed within an entry aperture and the guide body positioned in a selected orientation using the fixing mechanism to provide simple mounting of the trajectory guide. In some instances, the engagement surfaces may be fixed within the entry aperture and the guide body fixed in a selected orientation with a single fixation motion.

46 Claims, 3 Drawing Sheets

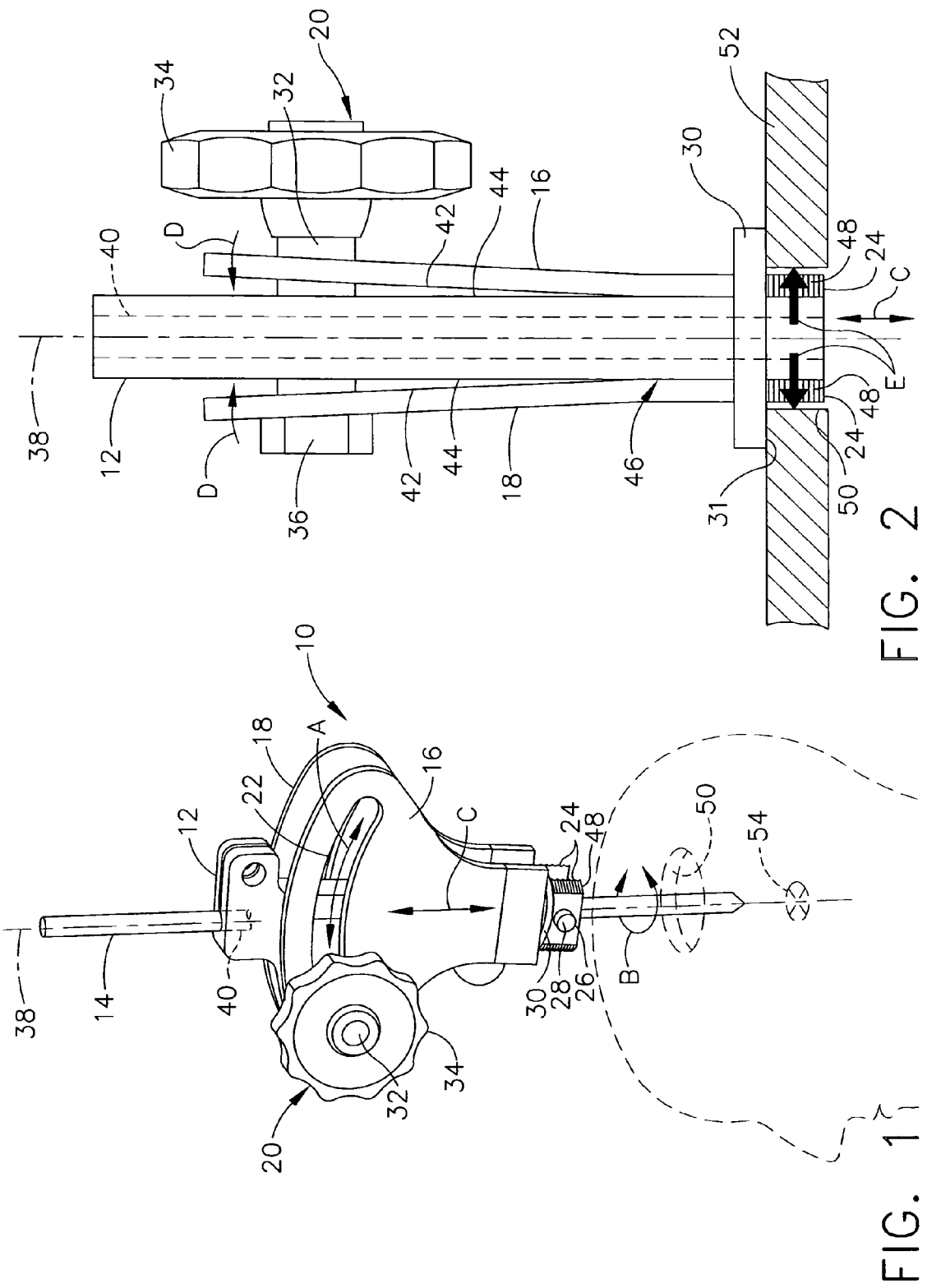

TRAJECTORY GUIDE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to surgical instruments.

2. Description of the Background of the Invention

Trajectory guidance systems are used in surgical procedures to create a stable guide for an operator, such as a surgeon, to increase precision of movement of a work instrument within confines of a highly sensitive region, such as a brain. The system includes a trajectory guide, which defines a stabilized trajectory to precisely guide a work instrument, such as a probe or other surgical instrument, toward a selected position in the body beyond the trajectory guide.

Many trajectory guidance systems are framed guidance systems, which include a large mounting frame that is fixedly mounted to an exterior side of a patient's skull with screws and pins surrounding an entry aperture, or "burr hole," through the skull. An adjustable guide member, such as a ball and socket with a guide bore, is carried by the frame adjacent or above the burr hole. The surgeon adjusts the guide member within the fixed frame so that the guide bore is axially aligned along a trajectory selected to precisely guide a surgical tool through the entry aperture toward a selected point on an interior side of the skull.

Other known trajectory guidance systems include frameless guidance systems, which dispense with the mounting frame described above, and rather use a small base portion with a guide member having a central bore therethrough. The base portion is secured with screws or bolts to the patient's skull over an entry aperture therethrough. A guide/holding tool is rotatably mounted to the base and includes an arcuate guide rail spaced above the base. A guide holder defining a guide bore is slidably carried by the arcuate guide rail whereby the guide bore circumscribes a range of trajectories that extend through the central bore and the entry aperture.

In another frameless guidance system, the base portion has an externally threaded stud and a central bore therethrough, wherein the stud screws directly into the entry aperture through the skull. The trajectory defined by the guide is adjusted by means of a removable ball and socket joint above the entry aperture.

Both the framed and frameless guidance systems previously known require at least a first procedure to attach the frame or base to the patient and a second procedure to fix the trajectory guide in a selected orientation with respect to the patient. Further, the angular range of adjustable motion of the trajectory may be limited by the size of the entry aperture because the pivot point of the trajectory is generally outside the entry aperture. Thus, a larger, more invasive entry aperture may be needed if a larger angular range of adjustable motion is desired.

SUMMARY OF THE INVENTION

According to one aspect of the invention, a trajectory guide includes a first clamp member spaced from a second clamp member, a guide body pivotably connected to the first and second claim members and defining a guiding surface and a brake surface, the brake surface disposed between the first clamp member and the second clamp member, and a clamp. At least one of the first clamp member and the break surface define a convex surface engaged against the other of the first clamp member and the brake surface. Furthermore, the first clamp member and break surface diverge from a first end toward a second end and the first clamp member rolls against the brake surface along the convex surface. The clamp is disposed proximate the second end and configured to urge the first clamp member and the second clamp member together at the second end against the brake surface of the guide body and thereby lock the guide body in a selected position. A first engagement surface is associated with the first clamp member, and a second engagement surface is associated with the second clamp member. Each engagement surface is disposed proximate the first end. The first engagement surface separates from the second engagement surface and the first clamp member is simultaneously clamped against the brake surface at the convex surface to lock the guide body in response to the clamp urging the first clamp member and the second clamp member together at the second end.

According to another aspect of the invention, a surgical trajectory guide includes means for adjustably defining a trajectory, means for releasably locking the defining means, and means for lockingly engaging a surface that defines an entry aperture. The locking means simultaneously locks the defining means in a selected position and urges the engaging means toward the surface.

According to a further aspect of the invention, a method of securing a surgical trajectory guide to a patient in a fixed orientation is disclosed. The trajectory guide includes a guide carried by a body and a fixation mechanism, wherein the guide is angularly adjustable with respect to the body and lockable by the fixation mechanism. The method includes the steps of inserting a first end of the body into an entry aperture in a skeletal member of the patient, selecting an angular orientation of the body with respect to the entry aperture, and selecting an angular orientation of the guide with respect to the body. The method further includes the step of simultaneously fixing the body in the selected rotational orientation within the entry aperture and locking the guide in the selected angular orientation with the fixation mechanism.

According to a still further aspect of the invention, a surgical trajectory guide includes a guide body defining a guide surface, a first engagement member, a second engagement member, and a fixing mechanism. The engagement members are associated with the guide body and adapted to be received within an entry aperture in a surgical patient, and the fixing mechanism is associated with the engagement members. The fixing mechanism moves the first engagement member away from the second engagement member, whereby the engagement members may be forced against an inside periphery of the entry aperture to fix the surgical trajectory guide to the surgical patient.

Other aspects and advantages of the present invention will become apparent upon consideration of the following detailed description.

BRIEF DESCRIPTION OF THE DRAWINGS

FIG. 1 is an isometric view of a trajectory guidance tool according to one embodiment of the invention shown in relation to a surgical patient;

FIG. 2 is an edge view of the trajectory guidance tool in an operable position within an entry aperture in a skull of a surgical patient shown partly in cross-section;

DETAILED DESCRIPTION

Figure 3:
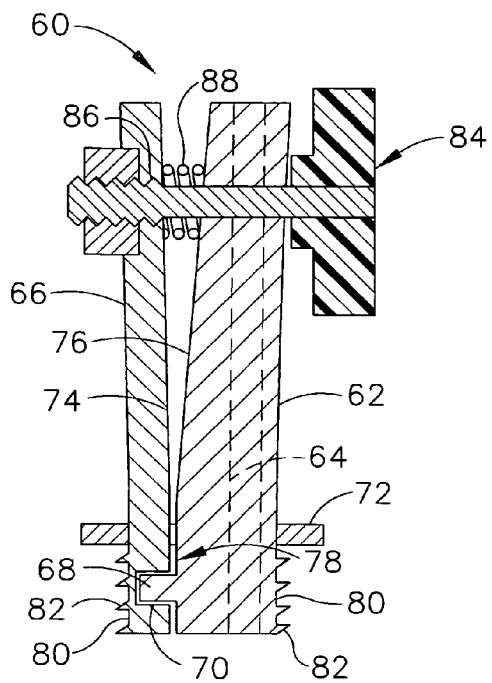
FIG. 3 is a cross-sectional view of a trajectory guidance tool according to another embodiment of the invention.

As shown in FIGS. 1 and 2, a trajectory guidance tool 10 includes an angularly adjustable guide 12 for adjustably and selectively defining a trajectory for a work instrument 14 pivotably secured between an opposing pair of clamping surfaces, such as opposing interior faces of a first plate 16 and a second plate 18, and a setting mechanism 20 for releasably locking the guide in a selected angular position with respect to the first and second plates. Each plate 16, 18 has a guide track, such as an arcuate slot 22 disposed along a top end thereof, for slidably guiding the guide 12 about a pivot point and an engagement arm 24, such as a narrow flange, disposed at a bottom end thereof for lockingly engaging a surface defining an aperture or other opening. Each plate 16, 18 also includes a blind bore or an aperture 26 extending at least partly through the engagement arm 24 from an interior face thereof. The guide 12 is connected to the plates 16, 18 at the pivot point, which in one embodiment is defined by two axially aligned studs 28 that protrude from two respective opposite sides of the guide at a bottom end thereof into the respective apertures 26. The studs 28 are pivotally disposed within the apertures 26, thereby allowing the guide 12 to pivot about an axis through the studs along an arcuate path A between the first and second plates 16, 18. A retention member 30, such as a spring wire, retention ring, cross brace, or washer, circumscribes the engagement arms 24 proximate the bottom end of the guide, thereby maintaining the first and second plates 16, 18 together and allowing the guide 12 to pivot about the studs 28. In one embodiment, the retention member 30 is a spring wire that urges the engagement arms 24 together. An axial stop surface 31 is defined in one embodiment by the retention member 30, such as by a lower surface of a washer or spring wire, although the axial stop surface may be defined by other protrusions and/or structures.

The setting mechanism 20 in one embodiment includes a screw clamp formed by a threaded bolt 32 slidably extending through the slots 22 between a turning knob 34 disposed on an outer side of the first plate 16 and a nut 36 disposed on an outer side of the second plate 18. The bolt extends through an aperture in the guide, thereby providing for angular movement of the guide about the studs when the bolt is moved between opposite ends of the guide tracks. Preferably, the nut 36 is rotationally restrained, such as by an engaging projection or by being at least partly slidably restrained within the respective slot 22, so that the screw clamp may be opened and/or closed with a single hand using the turning knob 34. Other mechanisms sufficient to squeeze and maintain the plates together in a condition to lock the guide in a selected angular configuration may also or alternatively be used, such as a removable C-clamp (not shown), a cam-type clamp (not shown) or, for example, the plates 16, 18 may be manually squeezed together to a selected clamping state and a clip, such as a common surgical scissor-clamp (not shown) having interlocking teeth or other inter-engaging single-use or reusable lock mechanisms, may be used to maintain the plates in the clamped state.

The guide 12 defines a trajectory 38 for the work instrument 14. In one embodiment, the trajectory 38 is defined by a central axial bore 40 extending through the guide 12 between a top end and a bottom end and between opposite side surfaces of the guide and passes through the pivot point such that every possible trajectory passes through the pivot point. In other embodiments, the trajectory 38 may be defined by the guide 12 in different relative positions, such as off-center or exterior to a side surface, and/or by different guide structures or surfaces, such as one or more projections (not shown). In the depicted embodiments, the bore 40 through the guide 12 defines a straight, axial trajectory 38 well suited for axial work instruments. In other embodiments (not shown), the guide 12 may define curved or non-axial trajectories, which may be useful for guiding non-axial work instruments. Further, the guide 12 may be adapted to define multiple simultaneous trajectories 38, such as by having more than one bore 40 and/or other guide surfaces.

Any of a number of work instruments 14 can be placed within the guide 12, such as tracked pointer devices that can be used to locate a point within the body of the patient, biopsy devices, screw drivers, and the like. In one embodiment, the work instruments 14 will be primarily cylindrical in shape and have an exterior diameter that is slightly less that the interior diameter of the passages within the guide 12. Other instruments may also be used, as contemplated above.

At least one of the plates 16, 18 pivots and clamps against the guide 12. In one embodiment, as best seen in FIG. 2, each plate 16, 18 has a convex inner surface 42 that diverges from a flat opposing side surface 44 of the guide member from the studs 28 toward the top end, thereby forming two fulcrum regions 46 proximate the retention member 30. The retention member 30, in one embodiment, is disposed between the fulcrum region 46 and the bottom end of the engagement arms 24, and in another embodiment is aligned with the fulcrum region. When the bolt 32 is tightened, the top ends of the plates 16, 18 are urged together, as shown by arrows D, at the fulcrum region 46, thereby squeezing and frictionally locking or clamping the guide 12 in a selected angular position while simultaneously pivoting the plates, such as by a rocking or rolling movement, about a second axis along the fulcrum region that is generally perpendicular with the axis through the studs 28, thereby causing the engagement arms 24 at the bottom ends of the plates to pivot or otherwise move apart, as shown by arrows E. In this manner at least one of the surfaces 42, 44 may be considered a braking surface or clamping surface.

In another embodiment, the location of the fulcrum area 46 can be such that as the setting mechanism 20 is tightened, the engagement arms 24 engage the sides of the burr hole and lock the trajectory guidance tool 10 rotationally in place before the surfaces 42, 44 fully engage the guide 12 so that the guide 12 can still be moved relative to the pivot point and may, in one embodiment, be held in place with light frictional pressure that can be overcome to position the guide. Thereafter, the setting mechanism 20 is further tightened to firmly hold the guide 12 in the chosen trajectory. Other pivoting arrangements are also possible. In another embodiment, for example, one or both of the plates 16, 18 may have flat opposing surfaces 42, and one or both side surfaces 44 of the guide 12 may be convex. Or, for example, only one of the plates 16 or 18 may pivot about the fulcrum area 46 and the other plate may be flush with the guide 12 or eliminated altogether. In yet another embodiment, the trajectory guidance tool 10 may include more than two clamping members which may, for example, be clamped against the guide 12 independently without actuating the engagement surfaces 50 and 48 and/or successively with the plates 16 and 18. The convexity of any one of the surfaces 42 and/or 44 may be arcuate or angular and preferably, although not necessarily, create the fulcrum region 46 nearer the engagement arms 24 than the top ends of the plates in order to form a longer moment arm between the fulcrum region and the setting mechanism. The convexity of the surfaces may be formed by an angle or curve in the respective surface and/or by one or more projections, such as elongate ridges or domes (not shown).

Preferably, the engagement arms 24 have surface gripping projections 48, such as ridges, striations, a roughened surface, hooks, or spikes, for example, on the outer surfaces thereof for grippingly engaging an inner peripheral surface of an entry aperture 50 in a skeletal member, such as a skull 52. Other shapes for the engagement arms 24, such as one or more rods or hooks, may also or alternatively be used.

In another embodiment, shown in FIG. 3, a trajectory guide tool 60 includes a guide body 62 defining a guide bore 64 therethrough and only one plate 66. The plate 66 is pivotably attached to the guide body 62 by a stud 68 disposed in a blind bore 70 and a retention ring 72. The plate 66 has a flat clamping surface 74 that opposes a convex brake surface 76 on the guide body, thereby defining a single fulcrum area 78 about which the plate and guide body 62 can pivot or rock similarly as described above. An engagement portion 80 is defined at a bottom end of each of the plate 66 and the guide body 62 and includes gripping members 82, such as spikes or ridges, for gripping an opposing surface. A screw clamp 84 similar to the screw clamp shown in FIGS. 1 and 2 slidingly disposed in a guide track 86 proximate a top end of the plate 66 allows a user to simultaneously lock the guide body 62 against the plate in a selected angular position and to fix the engagement portions 80 against an aperture wall as described previously. In addition, the plate 66 and guide body 62 are biased toward a selected position. In one embodiment, a biasing member 88, such as a spring disposed between the plate 66 and the guide body 62, urges the same toward an unclamped or unlocked position. In another embodiment (not shown), the plate 66 and guide body 62 may be biased toward a clamped or locked position.

Figure 4:
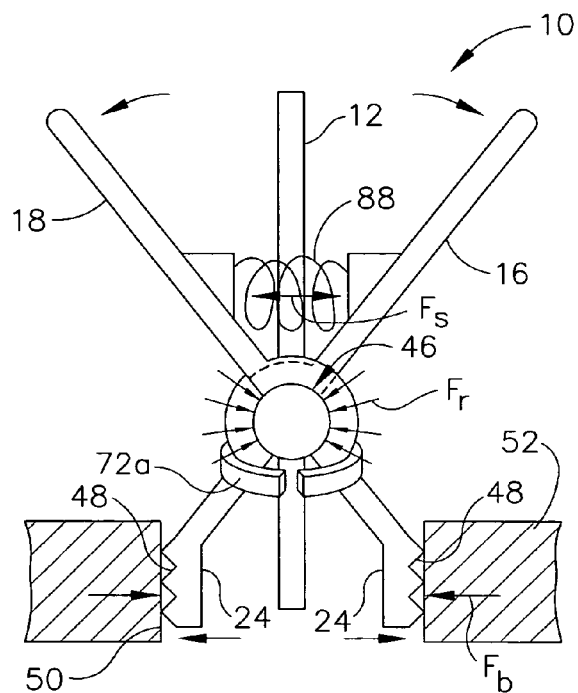
FIG. 4 is a schematic view in partial cross section of a trajectory guidance tool according to still another embodiment of the invention.

In a further embodiment, shown schematically in FIG. 4, a trajectory guide tool 10 has a single fulcrum region 46 adapted to work in a scissors-type fashion, whereby the engagements arms 24 move away from each other in response to the plates 16 and 18 moving away from each other, as shown by the arrows in FIG. 4. Conversely, when the plates 16 and 18 move toward each other, the engagement arms 24 also move toward each other. A spring 88 or other urging mechanism may be associated with the trajectory guide tool 10, such as being placed between the plates 16 and 18, to continually urge the engagement arms outwardly, which automatically maintains the trajectory guide tool in a fixed and clamped position inside the entry aperture 50. To disengage (or to initially insert) the trajectory guide tool 10 from the entry aperture 50, the user needs only to squeeze the plates 16 and 18 together in order to disengage the engagement arms 24 from the peripheral surface of the entry aperture. The guide 12 may be adapted to be pivotably adjustable in any manner suggested herein, and the trajectory guide tool 10 may be adapted to clamp the guide 12 in a selected orientation with the same motion or with a different motion than the motion described above to urge the engagement arms 24 into engagement with the entry aperture 50. For example, the plates 16 and 18 or the fulcrum region 46 may be adapted to cause the guide 12 to be clamped into a fixed position when the engagement arms 24 are spaced apart from each other in the fixed position. In one embodiment, the fulcrum section 46 is defined by a round or ball-shaped region of the guide 12. Preferably, although not necessarily, the guide 12 pivots about a point, or pivot point, located at a center of the ball-shaped section of the guide 12 such that the pivot point is independent of what direction the guide is pointing. In another embodiment, the pivot point of the guide 12 is outside of the guide. A resilient retainer, such as a spring wire 72a, is wrapped around the engagement arms 24 and urges the engagement arms 24 together, which eases insertion of the engagement arms into the entry aperture 50. Preferably, the force of the spring wire 72a is low, i.e., just enough to hold the trajectory guide tool 10 together in order not to fall apart. Once disposed in the entry aperture 50, the spring 88 urges the plates 16, 18 apart with a force Fs, and the peripheral wall of the entry aperture 50 urges against the engagement arms 24 with a force Fb, which together cause the plates 16, 18 to clamp against the fulcrum region 46 of the guide 12 with a breaking force Fr to fix the guide in position with respect to the plates 16, 18 and the entry aperture 50.

Figure 5:
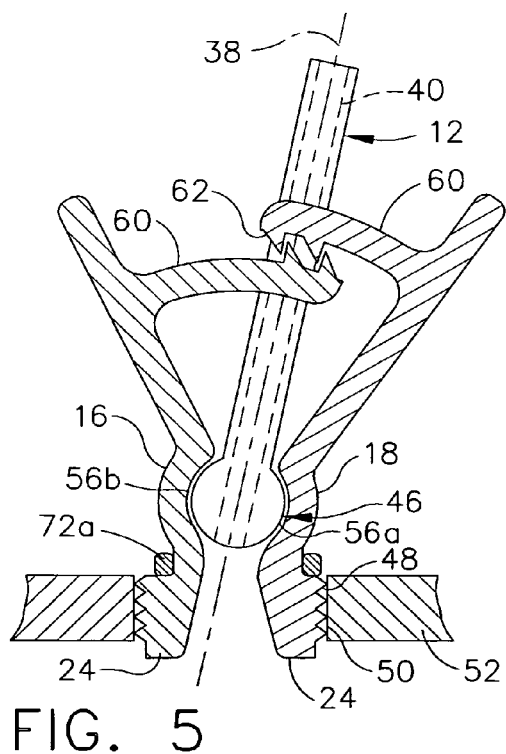
FIG. 5 is schematic cross-sectional view of a trajectory guidance tool according to a further embodiment of the invention.

In yet another embodiment shown schematically in FIG. 5, the guide 12 may be pivotably connected to one or both of the plates 16, 18 at a fulcrum region 46 defined by one or more ball and socket joints 56a, 56b whereby the guide may pivot about multiple axes to allow pivotal movement in more than one degree of freedom with respect to the plates. The guide 12 defines a spherical ball portion and the plates 16, 18 define complementary sockets that rotationally receive the ball portion therebetween. The sockets in the plates 16, 18 are maintained together about the ball portion of the guide by a resilient retainer, such as a spring wire 72a as described previously, or by another known mechanism, such as the retention member 30 (not shown). Preferably, the plates 16 and 18 have an unclamped state that allows selective pivotable adjustment of the guide 12 and a clamped state that fixes the guide in a selected position. Also preferably, the plates 16, 18 are arranged to cause the engagement arms 24 to spread outwardly when in the clamped state in order to fixedly engage the peripheral surface of the entry aperture 50 with the same motion used to clamp the guide in the selected position. The plates 16, 18 clamp against the ball portion of the guide 12 in the clamped state in a similar manner as described above. The ball and socket mechanism may also or alternatively include one or more three-dimensional extensions (not shown) to help maintain and guide the plates 16, 18 together with the ball portion of the guide 12. Opposing resilient locking arms having slidably engaging interlocking teeth 62, shown schematically at 60, similar to a common surgical scissor-clamp is another mechanism that may be used for locking the plates 16, 18 in the clamped state. The locking arms 60 may be adapted to be repeatedly locked and unlocked or may be adapted to be locked only once, after which the arms must be broken or destroyed in order to unclamp the plates 16, 18.

Figure 6:
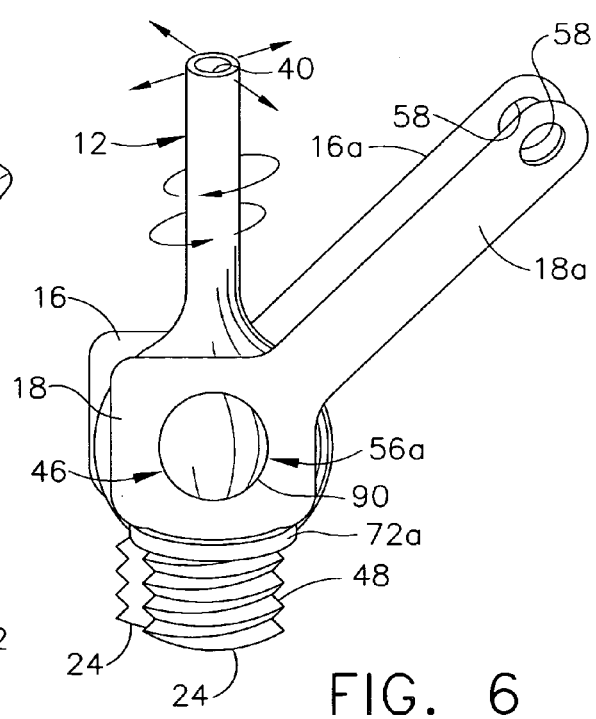
FIG. 6 is a schematic isometric view of a trajectory guidance tool according to yet another embodiment of the invention.

In a further embodiment shown in FIG. 6, each plate 16, 18 has an opening 90 therethrough defining a socket portion of a ball and socket joint 56a, 56b which pivotably receives the ball portion of the guide 12. A spring wire 72 resiliently retains the plates 16, 18 together against the ball portion of the guide 12, similarly as described previously. In this embodiment, handles 16a and 18a extend away from the respective plates 16, 18 to provide an easy grip surface for a user to squeeze together to simultaneously clamp the guide 12 in a selected position and to fix the engagement arms 24 within the entry aperture. When clamped together, the handles 16a, 18a may be releasably locked by any suitable mechanism, such as by a threaded bolt (not shown) extending through openings 58 in the handles 16a, 16b similar to the setting mechanisms 20 or screw clamp 84.

Figure 7:
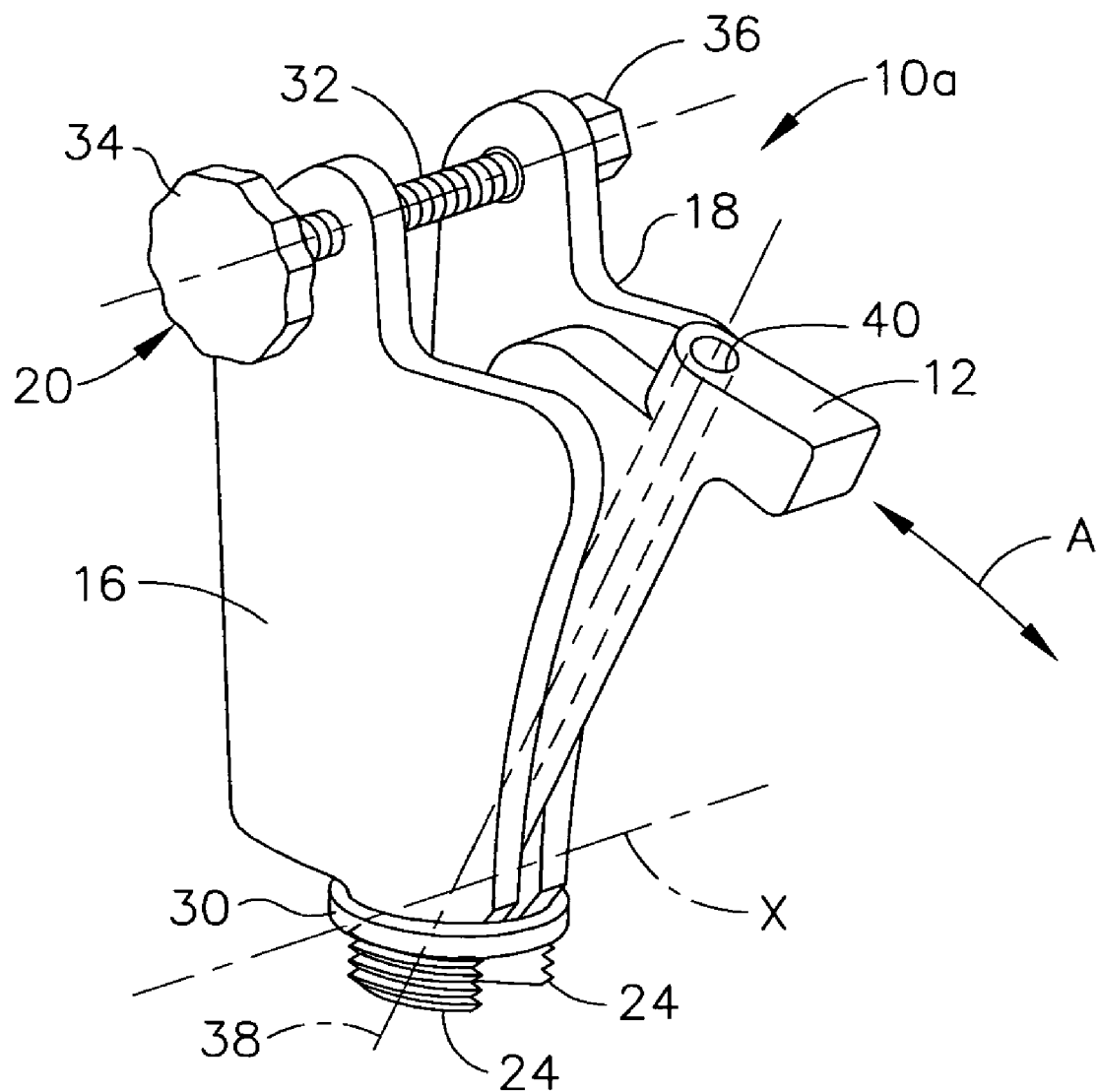
FIG. 7 is schematic isometric view of a trajectory guidance tool according to a still further embodiment of the invention.

In FIG. 7, another embodiment of a trajectory guidance tool 10a is generally similar to the embodiment shown in FIGS. 1 and 2, except that the guide 12 is not connected with the threaded bolt 32. Rather, the guide 12 pivots between the plates 16, 18 independent of the threaded bolt, which allows the guide a potentially larger range of pivoting motion A because the motion is not restrained by the arcuate length of the slots 22. Rather, the guide 12 could in some cases pivot any angular amount up to a complete revolution or more about an axis X through the engagement arms 24, thereby providing a full range of possible angular adjustment with respect to the plates 16, 18. Preferably, the threaded bolt 32 of the setting mechanism 20 is positioned radially beyond a top of the guide 12 such that the threaded bolt does not interfere with the angular movement of the guide. The axis X may intersect the bore 40 at perpendicular angles. Other portions of the trajectory guidance tool 10a are generally similar to the trajectory guidance tool 10 of FIGS. 1 and 2. An advantage of the trajectory guidance tool 10a is that the range of pivoting motion A of the guide member when the engagement arms 24 are fixed within an entry aperture 50 may be limited only by the size of the burr hole and the positioning of the engagement arms therein.

In one method of using a trajectory guidance tool of the present invention, such as the trajectory guide tool 10 of FIGS. 1 and 2, a single entry aperture 50 is formed in a skeletal member 52, such as a skull, to provide an access trajectory 38 to a desired work point 54 disposed inside the skull. A user, such as a surgeon (not shown), places the engagement arms 24 into the entry aperture 50 with the axial stop surface 31 disposed on an exterior side of the skull. With the setting mechanism 20 in a loose or un-fixed state, the surgeon rotates the trajectory guidance tool 10 about an axis passing through the entry aperture 50, as shown by arrows B, and pivots the guide 12 along path A about an axis through the studs to a selected angular position with respect to the plates 16, 18, thereby defining a selected trajectory 38 through the bore 40 toward the work point 54 within a cone of infinite possible trajectories (not shown). Because the work instrument 14 projects beyond the guide 12, the user can manipulate trajectory guidance tool 10 by manipulating the work instrument 14 to rotate the trajectory guidance tool 10 and also adjust the angle of the guide 12. If desired the surgeon may also adjust the trajectory 38 axially within the entry aperture 50 by moving the engagement arms 24 into and/or out of the entry aperture, as shown by arrows C. Once the desired trajectory 38 is defined, the surgeon then tightens the bolt 32, such as by rotating the knob 34 with one hand while holding the plates 16, 18 with the other hand, which simultaneously fixes the trajectory guidance tool 10 to the skull by engaging the gripping projections 48 on the engagement arms 24 outwardly against the inner periphery of the entry aperture 50 through the skull 52 and locks the guide member 12 in the selected angular position by clamping between the plates 16, 18. The trajectory 38 may subsequently be changed by loosening the screw clamp with one hand, re-adjusting the rotation, angle, and/or axial position of the guide with the other hand, and then re-tightening the screw clamp with the one hand, thereby re-fixing the trajectory with respect to the work point 54.

One possible advantage of some of the embodiments disclosed herein includes the ability to quickly and easily adjust the trajectory of the guide member about two degrees of freedom before fixing the trajectory guidance tool to the patient by separating and realizing the two rotational degrees of freedom along two independent axes. For example, in the trajectory guidance tool 10, a rotational orientation for the trajectory guidance tool is freely selected in any position inside the entry aperture 50 in a first degree of freedom by rotating the entire trajectory guidance tool along path B about an axis of rotation extending through the entry aperture that is approximately normal to the skull 52 (for example, the axis 38 as shown in FIG. 1) when the engagement arms are disposed in the entry aperture 50. The angular orientation of the guide member 12 may then be selected with a second, independent degree of freedom by rotation along path A about a pivot point defined by an axis through the studs 28, which in this embodiment is approximately perpendicular to the axis of rotation through the entry aperture, thereby allowing the user to select any desired trajectory line 38 within a cone of possible trajectories. The pivot point can be located somewhere inside the bone of the patient below the bone surface, such as approximately half-way through the thickness of the bone, whereby the guide member 12 has a maximum range of pivotal motion along the path A. Alternatively, the range of pivotal motion along the path A may be reduced by locating the pivot point on an exterior side of the bone surrounding the entry aperture 50.

INDUSTRIAL APPLICABILITY

The present invention may be used to provide a defined trajectory for a work instrument, such as a probe for a surgeon during a brain surgery operation. Although described generally in relation to surgical uses, other industrial applications may also be available where a user wishes to easily define a selected trajectory in relation to another object.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A trajectory guide comprising:
a first clamp member spaced from a second clamp member;
a guide body pivotably connected to the first and second clamp members and defining a guiding surface and a brake surface, the brake surface disposed between the first clamp member and the second clamp member, wherein at least one of the first clamp member and the brake surface defines a convex surface engaged against the other of the first clamp member and the brake surface, wherein the first clamp member and the brake surface diverge from a first end toward a second end and the first clamp member rolls against the brake surface along the convex surface;

a clamp disposed proximate the second end and configured to urge the first clamp member and the second clamp member together at the second end against the brake surface of the guide body and thereby lock the guide body in a selected position; and a first engagement surface associated with the first clamp member and a second engagement surface associated with the second clamp member, each engagement surface disposed proximate the first end;

wherein the first engagement surface separates from the second engagement surface and the first clamp member is simultaneously clamped against the brake surface at the convex surface to lock the guide body in response to the clamp urging the first clamp member and the second clamp member together at the second end.

2. The trajectory guide of claim 1, wherein the first engagement surface separates from the second engagement surface when the first clamp member travels toward the second clamp member at the second end.

3. The trajectory guide of claim 1, wherein the guide body is pivotably connected to the clamp surface along a first axis, and wherein the convex surface is convex about a second axis that is orthogonal to the first axis.

4. The trajectory guide of claim 1, further comprising a biasing member positioned to urge the first clamp member and the brake surface toward an unclamped position.

5. The trajectory guide of claim 1, wherein the guide body is angularly adjustable with respect to at least the first clamp member about a pivot point that is fixed in relation to the clamp member.

6. The trajectory guide of claim 5, wherein the first clamp member and the second clamp member restrain the guide body from angular adjustment when the first clamp member travels toward the second clamp member at the second end.

7. The trajectory guide of claim 5, wherein the clamp further comprises a resilient interlocking member that locks the first clamp member against the guide body.

8. The trajectory guide of claim 5, wherein the clamp further comprises a threaded member extending between the first clamp member and the second clamp member, the threaded member urging the first clamp member and the second clamp member together when the threaded member is rotated.

9. The trajectory guide of claim 8, wherein the first clamp member is defined by a first plate and the second clamp member is defined by a second plate.

10. The trajectory guide of claim 9, wherein a guide track is defined by the first and second plates a constant radial distance from the pivot point, the threaded member being slidably disposed in the guide track and interconnected with the guide body.

11. The trajectory guide of claim 8, wherein the guide body pivots independently of the threaded member.

12. The trajectory guide of claim 5, wherein the guide body is pivotable about a first axis, and wherein the first clamp member rocks with respect to the guide body about a second axis defined by the convex surface that is perpendicular to the first axis.

13. The trajectory guide of claim 12, further comprising a retainer maintaining the first clamp member at a maximum spacing from the second clamp member, wherein the retainer is disposed between the second axis and the first end.

14. The trajectory guide of claim 13, wherein the retainer defines a support surface disposed between the first end and the second end.

15. A surgical trajectory guide comprising:
means for adjustably defining a trajectory;
means for releasably locking the defining means; and
means for lockingly engaging a surface that defines an entry aperture;
wherein the locking means comprises a fulcrum defined between two opposed braking surfaces, a setting mechanism for urging the two opposed engaging surfaces together, and a retention means for restraining separation of the engaging means disposed between the fulcrum and the engaging means,
wherein the locking means simultaneously locks the defining means in a selected position and urges the engaging means toward the surface by clamping the two opposed braking surfaces against each other at the fulcrum in coordination with the retention means.

16. The surgical trajectory guide of claim 15, further comprising means for biasing the locking means toward a first locking state.

17. The surgical trajectory guide of claim 15, wherein the locking means and the engaging means comprises at most one fulcrum.

18. The surgical trajectory guide of claim 17, wherein the fulcrum comprises a ball and socket joint.

19. The surgical trajectory guide of claim 15, wherein the locking means and the engaging means comprise two fulcrums.

20. The surgical trajectory guide of claim 15, wherein the setting mechanism comprises a resilient interlocking member.

21. The surgical trajectory guide of claim 20, wherein the setting mechanism further comprises a second resilient interlocking member that interlocks with the first resilient interlocking member.

22. The surgical trajectory guide of claim 15, wherein the setting mechanism comprises a screw clamp.

23. The surgical trajectory guide of claim 15, wherein the locking means comprises a first wall spaced from a second wall, each wall extending between a first end and a second end, respectively, wherein the first wall and the second wall clamp the defining means therebetween.

24. The surgical trajectory guide of claim 23, wherein the first wall and the defining means define a fulcrum region therebetween.

25. The surgical trajectory guide of claim 24, wherein the second wall and the defining means define a second fulcrum region therebetween.

26. The surgical trajectory guide of claim 24, wherein the engaging means comprises at least one flange extending from the first end of one of the walls and a means for gripping the surface.

27. The surgical trajectory guide of claim 26, wherein the defining means is pivotally connected with the locking means.

28. The surgical trajectory guide of claim 27, wherein the defining means pivots about a first axis and the first and second walls rock about a second axis.

29. The surgical trajectory guide of claim 28, wherein the first axis is perpendicular to the second axis.

30. The surgical trajectory guide of claim 29 wherein the setting mechanism comprises a clamp.

31. The surgical trajectory guide of claim 29, wherein the setting mechanism further comprises second means for guiding the defining means about the first axis.

32. The surgical trajectory guide of claim 31, wherein the defining means comprises a body defining a bore that is adapted to guide a surgical tool along a selected trajectory.

33. The surgical trajectory guide of claim 31, wherein the second guiding means comprises an arcuate path.

34. The surgical trajectory guide of claim 15, wherein the defining means comprises a first axis and another axis extending through the entry aperture, whereby two degrees of freedom may be defined by independent rotational adjustment about the first axis and the other axis when the engaging means is disposed in the entry aperture.

35. A method of securing a surgical trajectory guide to a patient in a fixed orientation, the trajectory guide comprising a guide carried by a body and a fixation mechanism, the guide being angularly adjustable with respect to the body and lockable by the fixation mechanism, the method comprising:
  inserting a first end of the body into an entry aperture in a skeletal member of the patient;
  selecting an angular orientation of the body with respect to the entry aperture;
  selecting an angular orientation of the guide with respect to the body; and
  simultaneously fixing the body in the selected rotational orientation within the entry aperture and locking the guide in the selected angular orientation with the fixation mechanism by clamping the body against the guide to prevent angular adjustment of the guide with respect to the body and simultaneously urging, the first end of the body apart against an inner periphery of the aperture.

36. The method of claim 35, wherein the step of selecting an angular orientation of the guide further comprises the step of pivoting the guide about an axis that is fixed with respect to the guide and the body.

37. The method of claim 35, wherein the step of clamping further comprises the step of rocking the body about a convex surface against the guide.

38. The method of claim 37, wherein the step of fixing further comprises the step of pivoting the body with respect to the guide about a fulcrum spaced between opposite ends of the body.

39. The method of claim 37, wherein the step of fixing further comprises the step of pivoting the body with respect to the guide about two fulcrums spaced between opposite ends of the body.

40. The method of claim 39, wherein the step of fixing further comprises the step of separating opposing engagement surfaces.

41. A surgical trajectory guide comprising:
  a guide body defining a guide surface, wherein the guide surface comprises a bore through the guide body;
  a first engagement member and a second engagement member, the engagement members being associated with the guide body and adapted to be received within an entry aperture in a surgical patient, wherein at least one of the engagement members includes gripping projections on an outer surface thereof; and
  a fixing mechanism associated with the engagement members, wherein the fixing mechanism comprises a fulcrum defined by the guide body and engaged against the first engagement member;
  wherein the fixing mechanism squeezes the first engagement member against the fulcrum of the guide body and moves the first engagement member away from the second engagement member by rolling over the fulcrum, whereby the gripping projections of the engagement members may be forced against an inside periphery of the entry aperture to securely angularly fix the surgical trajectory guide to the surgical patient, and whereby the bore defines a trajectory into the entry aperture from an exterior.

42. The surgical trajectory guide of claim 41, further comprising a fulcrum area associated with at least one of the first engagement member and the second engagement member, wherein the fixing mechanism pivots the respective engagement member about the fulcrum area to move the first engagement member away from the second engagement member.

43. The surgical trajectory guide of claim 42, further comprising a clamp surface associated with at least one of the first engagement member and the second engagement member, wherein the clamp surface lockingly engages the guide body when the first engagement member is moved away from the second engagement member.

44. The surgical trajectory guide of claim 43, wherein the guide body pivots with respect to the clamp surface about an axis other than the fulcrum area.

45. The surgical trajectory guide of claim 44, further comprising a second clamp surface, wherein the first clamp surface is associated with the first engagement member and the second clamp surface is associated with the second engagement surface, and wherein the guide body is disposed between the first clamp surface and the second clamp surface.

46. The surgical trajectory guide of claim 41, wherein the guide body is pivotally associated with at least one of the first and second engagement members by way of a ball and socket connection.

* * * * *